United States Patent [19]

Carpenter

[11] Patent Number: 4,576,772
[45] Date of Patent: Mar. 18, 1986

[54] CATHETER WITH OPTIMUM RESISTANCE TO BENDING AND METHOD OF MANUFACTURE

[75] Inventor: George J. Carpenter, Southbridge, Mass.

[73] Assignee: Warner-Lambert Technologies, Inc., Morris Plains, N.J.

[21] Appl. No.: 632,940

[22] Filed: Jul. 20, 1984

[51] Int. Cl.⁴ .................. B28B 1/48; B29D 19/08
[52] U.S. Cl. .................. 264/154; 264/259; 264/339; 604/280
[58] Field of Search .................. 604/280, 281, 264; 128/4.6; 264/339, 154–156, 127, 251, 259; 138/117, 119, 125, 132

[56] References Cited

U.S. PATENT DOCUMENTS 3,799,151 3/1979 Fukaumi .................. 128/6
3,923,937 12/1975 Piccioli et al. .................. 264/154 X
3,998,216 12/1976 Hosono .................. 128/6

Primary Examiner—Stephen C. Pellegrino
Attorney, Agent, or Firm—R. S. Strickler

[57] ABSTRACT

A multi-lumen fluid-tight catheter having optimum resistance to bending and method of manufacture. The catheter is notched about its periphery and along its length to create voids which are filled with a vulcanized polymeric material.

11 Claims, 4 Drawing Figures

CATHETER WITH OPTIMUM RESISTANCE TO BENDING AND METHOD OF MANUFACTURE

Background of the Invention

The present invention relates to catheters or flexible tubes and relates in particular to the distal or articulating end of flexible tubes which are incorporated into endoscopes and the like having a plurality of lumens or through bores providing conduits for articulating wires, glass fiber bundles, irrigation and vacuum channels in well-known fashion and for well-known purposes.

The flexible tube is usually a plastic spiral winding or links of plastic extrusion segments of a given hardness and a given resistance to bending and is frequently formed with voids defining indentations, notches or cut-outs along its length and about its periphery to create a vertabra-like structure to facilitate bending.

Prior art tubes are disclosed and described in U.S. Pat. Nos. 3,799,151 and 3,998,216 issued Mar. 26, 1974, and Dec. 21, 1976, to M. Fukaumi et al. and S. Hosono, respectively, both assigned on the face of each patent to Olympus Optical Company Ltd., Tokyo, Japan.

In the '151 patent a plurality of segments, such as segments 19 through 23, are hinged together to provide freedom to flex under control of flexing wires 26a and b.

In the '216 disclosure, a spiral winding 11 is covered by braid 15; links 13 and 13a overlay the braid and envelope 18 forms an outer shell.

SUMMARY OF THE INVENTION

The present invention provides a less complicated structure and one which lends itself to manufacturing simplicity.

Therefore, it is an object of the present invention to provide a flexible catheter or tube of simple design and optimum flexibility useful on the distal end of an endoscope.

It is a further feature of the invention to provide a novel method of decreasing the inherent resistance to bending of a plastic tube having a durometer hardness of the order of 50 to 60 on the D scale.

A further feature of the invention is the provision of a flexible tube comprising a combination of plastic materials of different durometer hardness effective to develop an optimum resistance to bending.

It is a further feature of the invention to provide a flexible catheter which is fluid-tight.

A method of fabricating a flexible tube embracing certain principles of the present invention may comprise the steps of providing a length of a plastic tube having a given hardness and a given resistance to bending, creating voids about the periphery and along the length of the tube to develop a vertabra-like structure and filling the voids with a vulcanizable polymeric material having a hardness when cured less than the hardness of said plastic tube whereby the resistance to bending of said tube is reduced.

An article embracing certain principles of this invention and produced by the practice of the novel process steps may comprise a catheter of a given length having a plurality of lumens, a plurality of voids formed in the periphery and along the length of the catheter to generate a vertabra-like structure, and a vulcanizable polymeric material disposed in said voids, filling said voids and rendering the voids fluid-tight.

Other features and advantages of the invention will become apparent from an examination of the succeeding specification when read in conjunction with the appended drawings, in which;

DESCRIPTION OF PREFERRED EMBODIMENT

Figure 1:
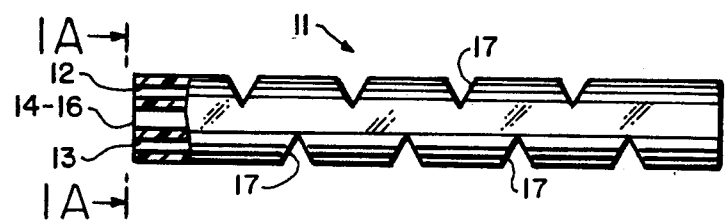
FIG. 1 is a combined side view and end view of a flexible catheter or tube.
Figure 1A:
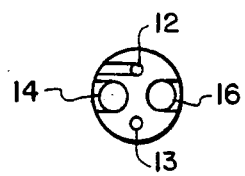

Referring now in detail to the drawings, the reference numeral 11 indicates a catheter or flexible tube having through bores or lumens 12, 13, 14 and 16.

The lumens 12 and 13 provide conduits or channels for wires or cables (not shown) which are used to flex the distal ends of a catheter in well-known fashion. Correspondingly, the lumens 14 and 16 provide channels for light guides and image-transmitting elements.

It is well within the contemplation of the invention to have numerous channels within the catheter as design characteristics and utility of the scope dictate. For example, channels for air, vacuum, forceps or irrigation are frequently included.

The tube 11 is fabricated of a plastic material, usually extruded, and resins such as polyethylene, polyvinyl chloride and the like are preferred, having a durometer hardness ranging from about 50 to 60 on the D scale.

The tube 11 is formed around its periphery and along its length with a pattern of voids 17—17 which take the form of cut-outs, notches or other openings. The voids 17—17 communicate with the channels 12, 13, 14 and 16 for reasons that will be more apparent hereinafter.

The voids 17 create what is termed a vertabra-like structure which adds flexibility to the catheter.

To control flexibility, the voids 17—17 are filled with a vulcanizable polymeric material such as polymers of silicones preferably in a formulation compounded to vulcanize at room temperature in about 24 hours.

Figure 2:
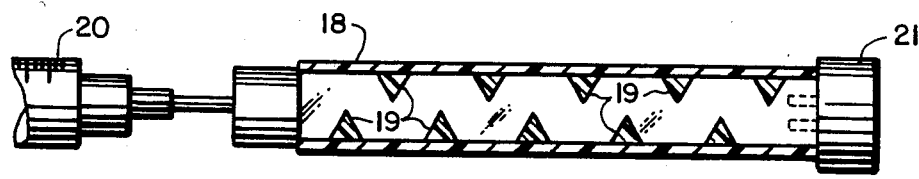
FIG. 2 is similar to FIG. 1 showing the introduction of polymeric material.
Figure 3:
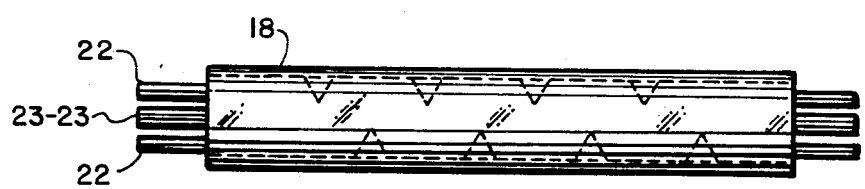
FIG. 3 shows the step of displacing excess polymeric material.

As indicated in FIG. 2, the vulcanizable polymeric material or filler, initially in a flowable condition, is injected by a syringe 20 or other suitable pump device into the lumens 12, 13, 14 and 16. Since the lumens are intersected by voids 17—17, the filler flows readily into the voids.

As is further apparent in FIG. 2, a transparent envelope or sleeve 18 is placed over the exterior of the catheter to confine the vulcanizable filler 19 within the voids 17 and to prevent overfilling.

It is preferable that the sleeve 18 be fabricated of polytetrafluoroethylene because of its low coefficient of friction.

An end plug 21 closes the right end of the catheter to confine the polymeric material within the catheter.

After all voids 17 are filled with vulcanizable material or filler 19, the cap or plug 21 is removed and the channels or lumens 12, 13, 14 and 16 are purged in that mandrels 22 and 23 are pushed through the lumens to displace excess polymeric material.

The resultant assembly, i.e., the combined vertabra-like structure and the filler 19, provides an articulatable catheter section or length that flexes readily with less stress and strain on the control wires as they are operated to deflect the distal end of the scope with which the catheter is used.

It is anticipated that a wide variety of embodiments of the present invention may be devised without departing from the spirit and scope of the invention as disclosed and claimed.

For example, the hardness of the plastic material from which the tube is fabricated relative to the hardness of the filler material is a matter of engineering choice, the only limitation being that the hardness of the filler material after curing be less than that of the tube or catheter.

What is claimed is:

1. A method of controlling resistance to bending in a multi-lumen catheter comprising the steps of providing a plastic tube of a given hardness, a given resistance to bending and a given length having a plurality of lumens, notching the tube about its periphery and along its length to create voids and to develop a vertabra-like structure, and filling the voids with a vulcanizable polymeric material having a hardness when cured less than the hardness of said plastic tube whereby the resistance to bending of said tube is reduced.

2. The method of claim 1 in which the notches are formed so as to intersect and communicate with the lumens.

3. The method of claim 2 plus the step of introducing the polymeric material through the lumens.

4. The method of claim 3 plus the step of enclosing the exterior of the tube in a transparent envelope to preclude overfilling the notches.

5. The method of claim 4 plus the step of capping or closing one end of each lumen.

6. The method of claim 5 plus the step of purging the lumens to displace excess filler material.

7. The method of claim 6 plus the step of purging the lumens by pushing mandrels through each lumen to displace said filler material.

8. The method of claim 7 plus the steps of curing the polymeric material and thereafter removing the mandrels and the envelope.

9. The method of claim 4 where the transparent envelope is polyethylene.

10. The method of claim 4 where the transparent envelope is polyvinyl chloride.

11. The method of claim 1 in which the vulcanizable material is a compound of silicone.

* * * * *